(12) United States Patent
Kelly

(10) Patent No.: US 8,857,433 B1
(45) Date of Patent: Oct. 14, 2014

(54) SAFETY GLASSES WITH HIDDEN DEPLOYABLE FACEPIECE

(71) Applicant: Robert Charles Kelly, Burlingame, CA (US)

(72) Inventor: Robert Charles Kelly, Burlingame, CA (US)

( * ) Notice: Subject to any disclaimer, the term of this patent is extended or adjusted under 35 U.S.C. 154(b) by 0 days.

(21) Appl. No.: 13/684,139

(22) Filed: Nov. 21, 2012

Related U.S. Application Data

(60) Provisional application No. 61/562,436, filed on Nov. 21, 2011.

(51) Int. Cl.
*A61M 11/00* (2006.01)
(52) U.S. Cl.
USPC ............ 128/206.24; 128/206.27; 128/206.28; 2/9

(58) Field of Classification Search
USPC .......... 128/206.21–207.13; 2/9, 15, 427, 428, 2/429
See application file for complete search history.

(56) References Cited

U.S. PATENT DOCUMENTS

| | | | | |
|---|---|---|---|---|
| 2,669,717 | A * | 2/1954 | Diggs | 2/9 |
| 4,821,340 | A * | 4/1989 | Johnson | 2/9 |
| 4,944,039 | A * | 7/1990 | Dietrich | 2/13 |
| 5,682,606 | A * | 11/1997 | Pospisil | 2/9 |
| 5,704,349 | A * | 1/1998 | Hubbard et al. | 128/206.19 |
| 5,797,146 | A * | 8/1998 | Matich | 2/424 |
| 5,956,119 | A * | 9/1999 | Gibbs | 351/158 |
| 6,216,695 | B1 * | 4/2001 | Ruben | 128/206.19 |
| 6,886,559 | B2 * | 5/2005 | McDonald et al. | 128/201.24 |
| 8,365,732 | B2 * | 2/2013 | Johnstone | 128/206.17 |

* cited by examiner

*Primary Examiner* — Steven Douglas

(57) ABSTRACT

The disclosure discloses an eye protection adjunct that provides protection to a person's eyes and resembles a normal pair of eyewear, but contains a hidden facepiece that deploys into a face protection system for the eyes, face, nasal and pharyngeal openings.

16 Claims, 5 Drawing Sheets

SAFETY GLASSES WITH HIDDEN DEPLOYABLE FACEPIECE

REFERENCES CITED WITHIN

U.S. Patent Documents
U.S. Pat. No. 1,279,884 9/1918 La Roche
U.S. Pat. No. 4,843,643 7/1989 Parissenti
U.S. Pat. No. 7,594,278 B2 9/2009 Huh
U.S. Pat. No. 5,424,787 6/1995 Zegarelli
U.S. Pat. No. 7,958,889 6/2011 Fernandez-Castro
U.S. Pat. No. 8,011,026 B2 6/2011 Stevens
U.S. Pat. No. 7,178,526 B2 2/2007 McDonald
U.S. Pat. No. D404,849 1/1999 Desy

BACKGROUND OF THE INVENTION

The need for safety adjuncts is well known, in particular those that protect a person's face and specifically those designed to protect the eyes, nose, mouth and their surrounding perimeters are an essential accessory in an effort to prevent irritation, injury or impairment, either temporary or permanent in nature while performing a multitude of tasks or while present in or passing through hazardous environments. Accidents occur even in the most cautious and well designed of settings, such as a laboratory or other workplace, and items such as goggles, safety glasses, filters, masks and other types of face or respiratory protection provide a much needed secondary basis of safeguarding one's self beyond standard operating procedures, common sense and rules. Outside of a controlled environment these types of safety devices become necessitous. As an example a person working in the outdoors may not be able to control how a rock will break, where chipped concrete or broken glass will fly, or the amount of dust a machine or process may produce in an uncontrolled environment. Other variables include such items as wind driven particles, droplets or objects, smoke, insects, pollen, rain, steam or gas from vehicles or vents, chemical spills, reactions, tanks releasing vapors, overheated mechanical equipment or explosions. In other environments, such as a medical setting (either in a facility or in the field) there is a need to protect ones self from a multitude of airborne or bloodborne pathogens, infectious body fluids that might splash, spray or splatter, germs, or infectious diseases (e.g. tuberculosis, H1N1), especially when certain types of medical treatment or procedures are performed in an enclosed location where space is limited and ventilation may be less than ideal.

This well documented need has been answered with a multitude of types of glasses or other eye protection, as well as an endless selection of masks, air filters, breathing apparatus or a combination thereof that allows the user to work in a potentially hazardous area. Many workplaces have rules in effect requiring the use of one type or another of these protective coverings. Additionally for most work performed in an outside environment (e.g. digging, tunneling, etc.) the need for these devices can be in many cases can be anticipated and prepared for in advance. The use of these types of safety adjuncts are often the result of a previous accident, but are also driven by common sense, preplanning, Unions, insurance needs, or Government laws and regulations (e.g. Occupational Safety and Health Administration). However; several problems continue to exist in this area of safety. Firstly, today in our society there remains an unmet need for the coverage of one's eyes, face and respiratory orifices (i.e. nose and mouth) in places and at times that were in the past never considered viable locations for such protection, and are not under any Government regulations or workplace rules. In these places it is of exigent need that this protection must be quickly and accurately deployed to prevent impairment, debilitation or injury. These places are just about anywhere and anyplace that people live, cohabitate, labor, travel, commute or leisure in, and may take place at any time of day or night. This need has been intensified with the advent of more chemicals, new strains of aerosol transmissible diseases (e.g. Avian Flu, Severe Acute Respiratory Syndrome) with pandemic possibilities, higher population density, an increase in man made and natural disasters and more importantly by an increase in the awareness of terrorism, including past acts and the potential for future acts of extremist acts in places that used to be assumed safe and secure by the general public. In a terrorist attack (e.g. dispersal of an airborne particulate or agent) there is little time to react without becoming potentially impaired. Terrorists and other radical factions are known to rely on the element of surprise in their attacks and are notorious for encompassing confusion and disorientation tactics in an effort to potentiate the effect as well as secure their escape. Many of the devices used by these guerillas in some manner emit smoke or vapors, sometimes visible, sometimes invisible but often with the goal of, the addition of; or the side effect of irritating the respiratory tract, impairing vision and debilitating humans. Post attack (e.g. explosives) there is the danger of long term effects such as exposure to asbestos or other carcinogens during rescue or response, and of more importance the possibility of a secondary device or attack immediately following the first attack.

This problem is especially important for those who work in the safety, law enforcement, military, or rescue field, where during or after an attack there is a duty to act and the simplest delay or impairment could greatly reduce the effectiveness of their response. While most of these first responders are trained in and are issued the necessary safety equipment, it isn't always readily available, suitable to carry or often there is a time factor in finding and donning the equipment (e.g. reaching in a pocket or bag).

An example of this would be a detail in a professional setting, where the assigned individuals must blend in with the general public and would be dressed in civilian clothing in a manner so as to be undistinguishable from the general public. As an example, a plain clothed police officer in a subway would not have the pockets to carry a full gas mask, or would be asked not to have one visible so as to alert or panic the public, but would be tasked to quickly respond to a person or persons who release a substance in an enclosed vestibule. In an instance like this there may only be seconds to subdue the assailant(s) and mitigate the problem. An officer in this instance must be able to keep constant visual contact with a perpetrator's whereabouts while protecting themselves, and at the same time not compromise their ability to operate a radio, draw a weapon, and move to confront, take cover, or move civilians out of harm's way. A secondary problem with safety adjuncts is the social and cosmetic concerns of the user. In an increasingly visible society (e.g. security cameras, social media, online videos, media phones, etc.) where expectations of privacy are decreasing and jobs more scarce and thus increasingly competitive, people wish to look their best whether in the public or private eye under all conditions. Many safety devices use clever coverings and colors in an attempt to make them socially acceptable, but many people feel uncomfortable wearing or carrying a mask and eye protection wherever they travel, and in some instances the appearance of them may serve to create worry or panic (e.g. on a train, bus or enclosed space). They will often forgo carrying or wearing them for the sake of vanity.

A third problem exists in the ability to recognize others who are wearing safety equipment. When a person's face and eyes are covered it is difficult to perceive who is behind such apparatus. This is especially critical in a field operation where there may be several similar groups working together (e.g. plainclothes agents) or under surveillance (such as a sniper operation) and there is a need for recognition. An example of this would be a crowded square in an area where it is common for the population to dress in similar garments. In a panicked and potentially hazardous situation it would be difficult from a distance to spot certain individuals, especially if engaging them in a situation where only a covered head and face were visible (e.g. gun fight). In such a case deploying face protection with a prearranged signaler sign (e.g. ultraviolet thread, logo, or chemical mark) could be the difference between life and death. Additionally the problem exists in many cases items where an immediate need for facial safety adjuncts may be misplaced, forgotten, hard to find, or have been used or contaminated and are no longer viable for use. In such instances the ability to have eye protection with a deployable mask filter would be advantageous and of great benefit not only to the user but also to those the user may be assisting (e.g. a patient with a compromised immune system who may become infected by the person rendering them aid).

Finally a device that solves the above problems must be inexpensive in order to be a practical choice.

Thus there is provided herein a solution for a cost efficient, concealable, disguisable, quickly and efficiently deployable safety adjunct that has the appearance of common eyewear, yet provides protection for the eyes, face and respiratory system with minimal disruption to the user and can have recognition signals.

SUMMARY OF THE INVENTION

In one aspect the invention provides for an ordinary looking pair of eyewear, with hinged earpieces, a frame and lenses of any type or color made from a material that meets requirements to be also worn as safety glasses and protect the orbits of the user. Within the device is a preformed cartridge that is unobtrusive in design.

In a second aspect, the cartridge is opened and deploys a hidden facepiece that covers the nasal and pharyngeal areas of the user and filters particulates from the surrounding air. The eyewear, in conjunction with the attached facepiece, also serves to protect the wearer's facial area from flying debris, particulates, splatter, etc. or certain chemicals and can be deployed with one hand.

In a third aspect the deployed facepiece has a design, logo or predetermined shape or chemical that acts as an identifier for the user or the user's colleagues, or the device contains another signaling or warning device such as a light emitting diode (L.E.D), infrared, laser, prism, hologram, or ultra-violet light.

The cartridge in any embodiment is a replaceable item so as to be cost efficient and allow for personalization.

In an additional aspect the device provides a kit that includes replacement cartridges and a selection of lenses or covers.

The device also solves the problems of carrying a second safety adjunct as it can be easily deployed should initial respiratory protection be compromised.

As the device is also contemporary in design and can be used as everyday eyewear (e.g. sunglasses), it is less likely to be forgotten and can be carried in places where storage is minimal (e.g. the beach).

In an additional aspect the invention provides a means of protection to one's eyes, face and airways and has a unique identifier visible when the facepiece is deployed, e.g. a logo shape, or other identifier (e.g. light or ultraviolet paint) to allow recognition by others. In each described aspect the process of protecting one's eyes, face, and airways can be accomplished in an expedient manner using one hand with minimal visual disruption to the user.

In summary those in the public service including law enforcement, rescue, and the military as well as the general public will benefit as well from the device, which mimics conventional eyewear (e.g. a pair of safety or sun glasses) but if necessary can be deployed in a subway, airplane or any situation where one would not normally carry combined eye and breathing protection but may suddenly find themselves in need of it. Furthermore those who may often forget breathing protection would benefit from having it in place when it is needed most or use it as a secondary device. Also, since the device deploys with one hand with minimal impairment of vision it allows the user to be more aware of other potential safety factors. Furthermore, users who normally wear some type of safety glasses, e.g. a building inspector or contractor will also benefit from having quick and efficient eye, face and airway protection and are less likely to lose it since it appears as a cosmetic accessory.

PRIOR ART

The teachings for eyewear and respiratory protection date back to the earliest of times. Only lately has technology advanced to the point where novelty and non-obvious solutions to the above stated problem again present themselves, and for the good of the public this recent answer is now offered forthwith.

Regarding the aforementioned one would be indecorous to not include in this document La Roche U.S. Pat. No. 1,279,884 who in 1918 perceived an eyeglass and mask concept. While the currently presented concept differs in so many respects (e.g. plastic, concealable, etc.) his vision represents the passion that drives others to improve the safety a quality of life for all.

Parissenti U.S. Pat. No. 4,843,643 brings the concept of protecting the face from the front by use of a rigid shield that connects to eyewear, however fails to address as does the device herein the need to inhibit particulate matter from entering the respiratory openings of the mouth and nose from ambient air.

Huh U.S. Pat. No. 7,594,278 shields the orbits and respiratory openings by use of a device that can be deployed with one hand, however fails to provide the non-obvious appearance of the presented invention.

In respect to the presented facepiece Desy U.S. Pat. No. D404,848 teaches a disposable face shield that has a curtain like effect, yet fails to consider and account for the physical characteristics that can create obstacles (e.g. nose) which in the above described problem would require the bending or folding of a supporting piece (e.g. metal insert) not to mention the difficulty in deploying the same in a urgent manner. Unless worn continuously prior to engagement any facepiece (or face shield) would cause a delay in positioning and doing so prior to use would have negative cosmetic effects, which the presented device addresses. The device as presented allows for a continuous attachment to a frame that encompasses the bridge of the nose and is deployed with a single hand.

Zegarelli U.S. Pat. No. 5,424,787 addresses the need for eyeglasses that are safety glasses with the attachment of a non-rigid mask. He teaches an attachment point built into the eyewear frame which allows for positioning and replacing a surgical mask adjunct but fails to address protection of the area below the bottom frame of the eyewear and above the flaring of the nose (e.g. cheekbones) which in the intended device brought forward is intentional in its means and scope as it lessens the chance for fluids or vapors, especially those dispersed in a manner as to cause harm (e.g. chlorine gas that convert to hydrochloric acid when mixed with water or sweat). Furthermore attachment pieces located on each side of the eyewear in front of the pinna may interfere with the user and not be cosmetically acceptable.

Fernandez-Castro U.S. Pat. No. 7,958,889 shows us a mask as a moldable attachment which again is a single piece with again a bendable support required to fit the bridge of the nose. The facepiece portion of the presented device differs in that it requires no molding by the user as it shapes itself when attached as described herein.

Stevens U.S. Pat. No. 8,011,026 teaches replaceable parts and continuous eye, face and respiratory protection but fails to address the need to have the nose and face exposed so as not to draw attention to same in a public environment (e.g. shopping center or airport) prior to its need and in fact if worn in many of the urban areas in the United States would draw an immediate response by the public and law enforcement officials.

McDonald U.S. Pat. No. 7,187,526 teaches a mask and harness system, in his case pneumatically opened against the manual operation of the device, but does educates that a facial protection system can be designed for economy of space and rapid deployment. He fails to address the need to carry such protection on one's self at all times as is offered within.

BRIEF DESCRIPTION OF THE DRAWINGS

FIG. 1 further references the facepiece cartridge 200, shown prior to being attached or deployed and consists of the facepiece holder 210, which is in part hollow in structure (so as to contain the facepiece 230 and securing strap(s) 240 which are shown in FIG. 4.), and has one it's interior edge protruding insertion tabs 215 that correspond in placement and are designed with the above described insertion holes 115. The Facepiece Holder 210 has on the top edge near it's center point a Release Tab 220 that is described further herein.

FIG. 7C shows the position of the support piece section(s) 250 in their final deployed position.

DETAILED DESCRIPTION OF THE INVENTION

Figure 1:
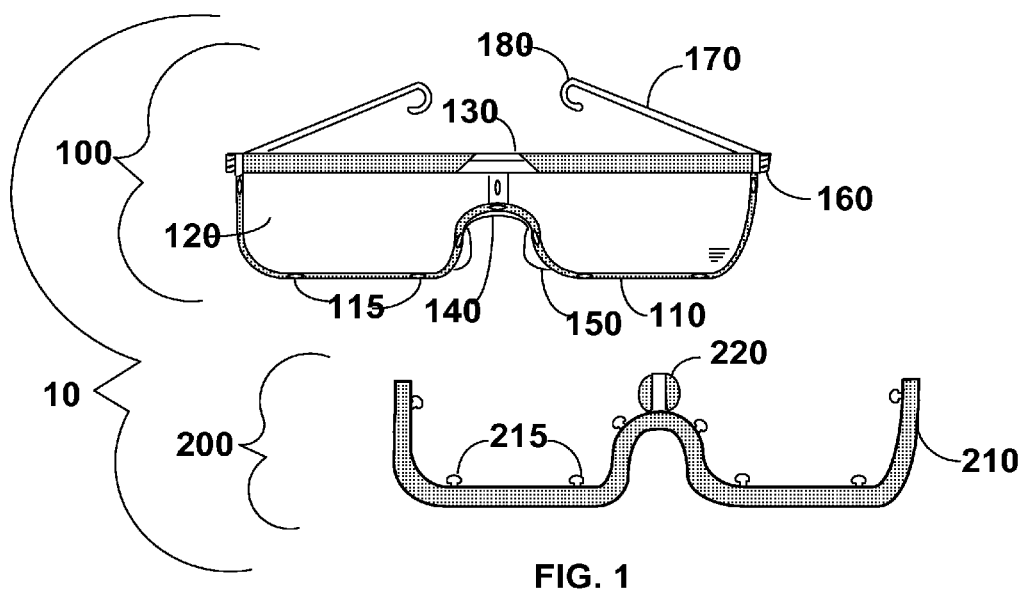
In FIG. 1 reference is made to the device 10 shown unassembled for simplicity and consisting of the frame 100 which is the main body of the device and the facepiece cartridge 200 which is a replaceable adjunct that attaches to it. The frame 100 consists of a rim 110 that is designed to hold the lenses 120 which can be inserted into or formed as part of it. The rim 110 has along its center, lower and side perimeter edges insertion holes 115, and on its topside a bridge 130 which may be straight or curved in design. Below the bridge 130 and centered between the rim 110 sides and lenses 120 is the nosepiece 140. The nosepiece 140 may be formed as part of the rim 110 as well, or as separate piece and having adjustable pad plates 150. On the outer edges of the frame 100 and attached to the rim 110 are the end pieces 160. The end pieces 150 are designed to accept the hinged earpieces 170, which have at each of their distal ends a curved bend 180.
Figure 2:
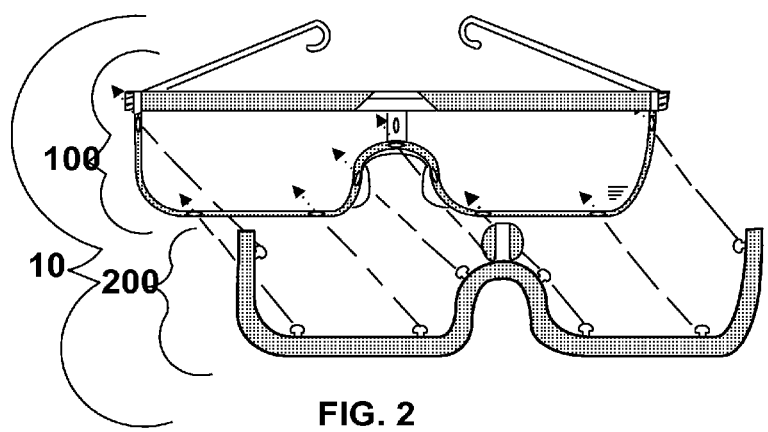
FIG. 2 again shows the device 10 with frame 100 and cartridge 200 aligning so in a manner so that the insertion tabs 215 will fit into the insertion holes 115 as to cause to two pieces to become a single device 10.
Figure 3:
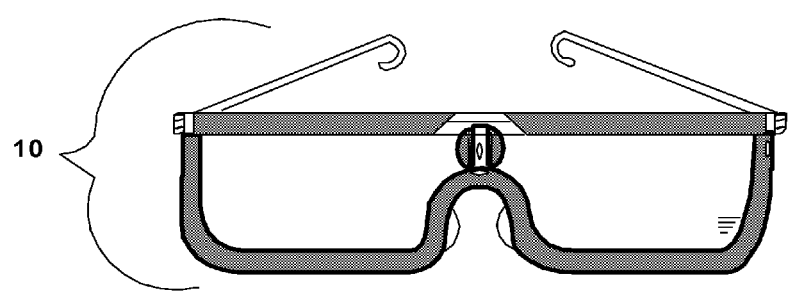
FIG. 3 depicts the invention as a single device 10.
Figure 4:
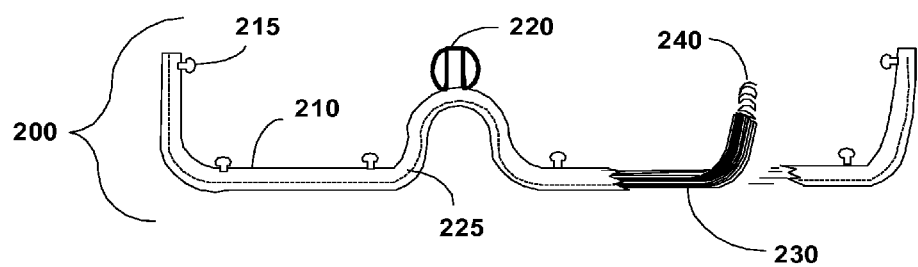
FIG. 4 depicts a view of the cartridge 200. In this view the facepiece holder 210 has a line of weakness 225 that will cause a separation when the release tab 220 is engaged. As the holder separates it one part will be held in place by the insertion tabs 215 and the other part will open as shown in the partial cutaway view to reveal the facepiece 230 and securing strap(s) 240.
Figure 5:
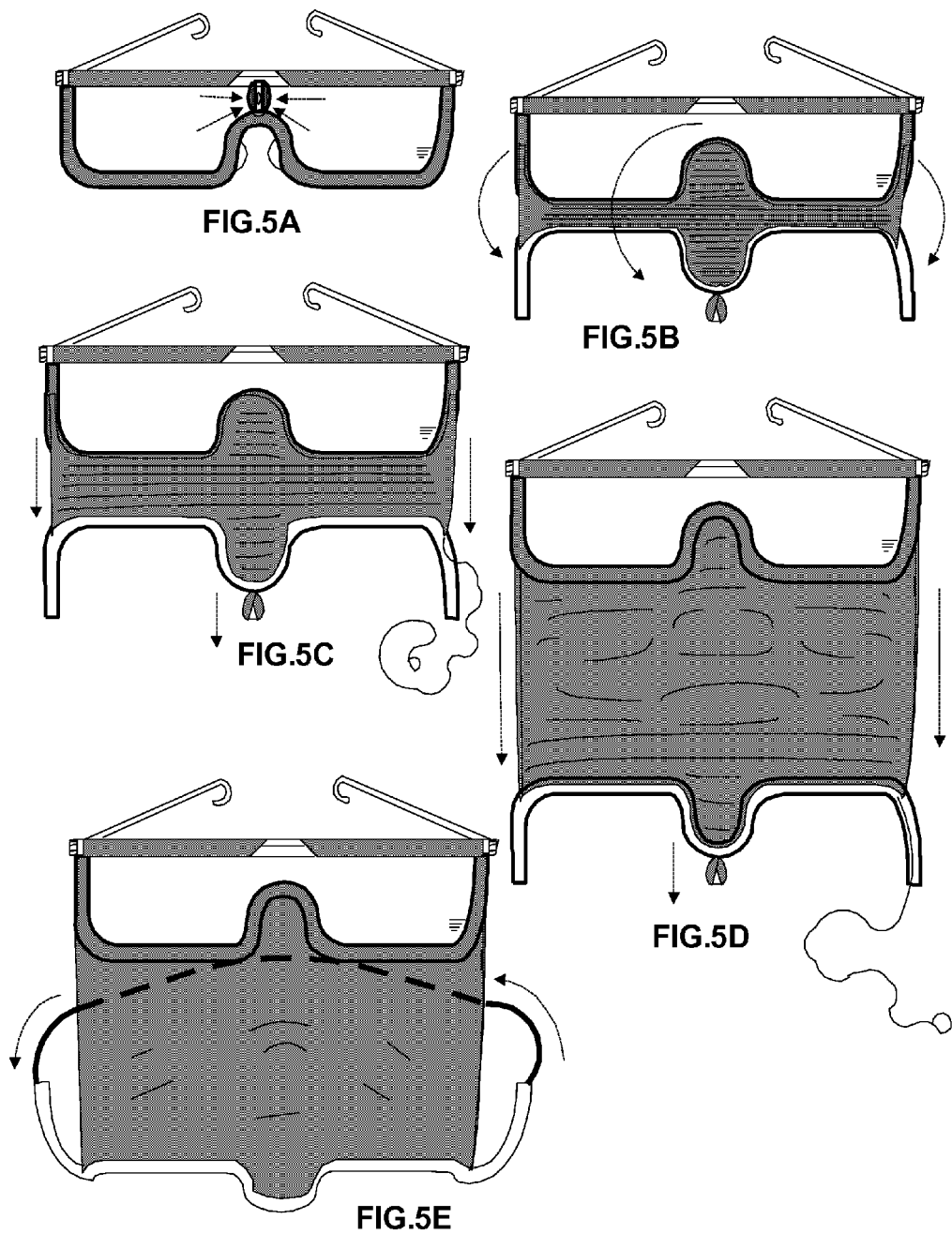
FIGS. 5A, 5B, 5C, 5D and 5E show the steps involved in deploying the facepiece.
Figure 6:
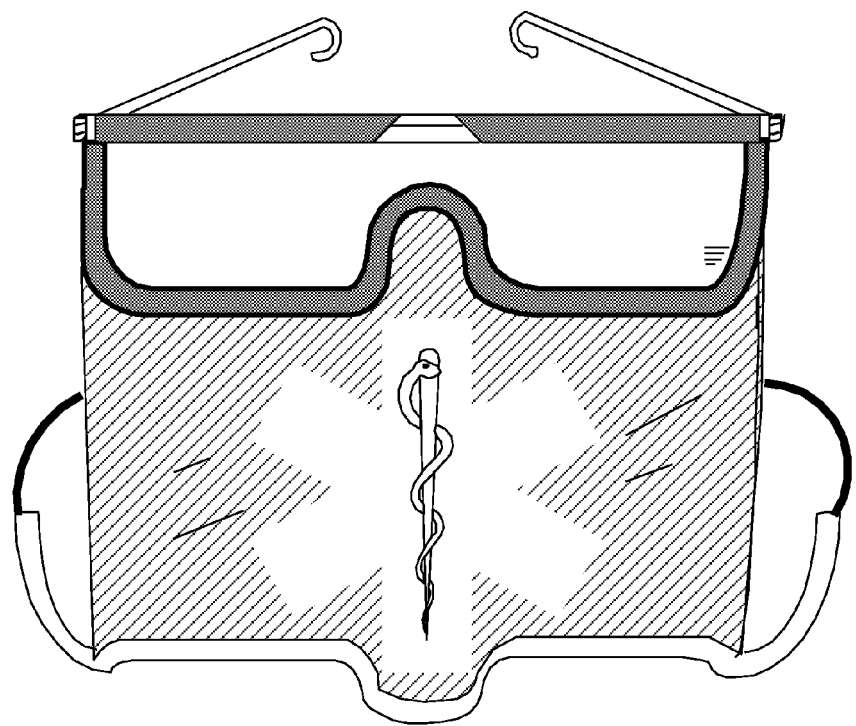
FIG. 6 depicts the device deployed revealing a hidden logo.
Figure 7A:
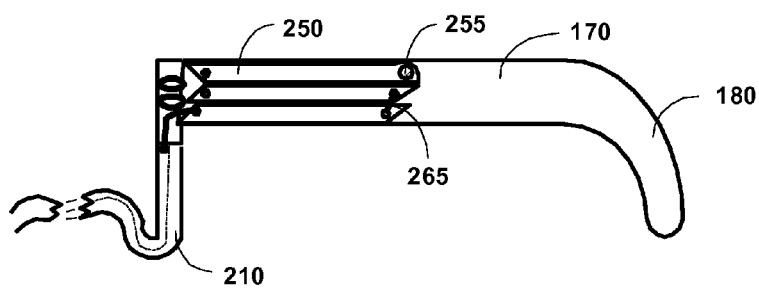
FIGS. 7A, 7B, AND 7C depicts an alternate method of supporting a facepiece. Displayed is a side view of a hinged earpiece 170 with a curved bend 180. Shown for illustrative purposes in FIG. 7A only is a cutaway view of the facepiece holder 210. Further depicted are support piece section(s) 250, each of which has a connecting point 260 and a joining connector 265. The top supporting section is joined to the hinged earpiece 170 with a pivot point 255.
Figure 7B:
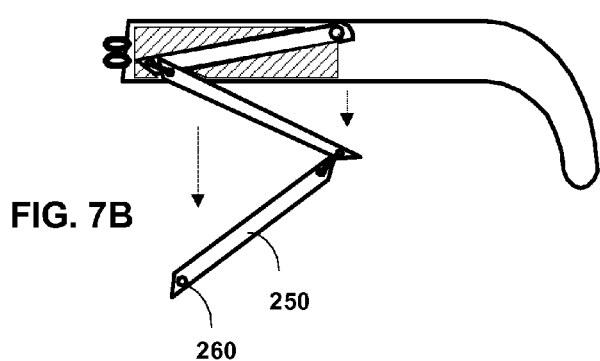
Figure 7C:
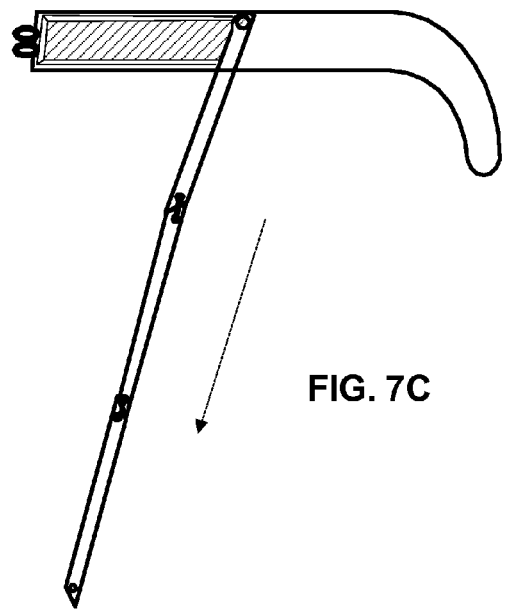

The present invention provides for a conventional eyewear device 10 to be worn on a person's face under a variety of conditions. The device 10 has a frame 100 that is consistent in design with eyewear in that it is proportionate in size with a user's face either by design or by means of adjustment (e.g. tab insert) or model size (e.g. small, medium, large, etc.) and allows for minimal restriction of a user's vision when worn. The parts of the frame 100 described below consists firstly of a rim 110 which forms an outside border and provides attachment points which are described herein. Those familiar with the art can appreciate the border formed can be similar to conventional eyewear in that it may be square, rounded, rectangular, or of any size or shape as to adequately cover one's orbits and eyes. The rim 110 in a preferred embodiment is constructed of lightweight nylon, but in other embodiments may be constructed of plastic, polycarbonate, polyurethane, copolymers, composites, metals (e.g. aluminum), rubber, Teflon, silicone or other polymers or blends or combinations of materials that may allow for strength, impact resistance, twisting, and withstands exposure to chemicals, heat, cold, conductive or other adverse environments depending on the use; and may be formed so as to create a seal to the user's face (e.g. rubber gasket or sponge) and also in another embodiment may have ventilation holes to help prevent fogging. It may be manufactured as a single solid piece or hollow as two pieces that snap together as described below to allow for inserting adjuncts as described below. In some cases, for example for use in general commercial markets, the device is designed around regular glasses, sunglasses, or designer glasses and can snap on to existing designs.

The design of the rim 110 also allows for insertion holes 115 which allow attachments as defined below. The rim 110 is designed in such a manner as to allow for the holding in place lenses 120 that may be single, double or have multiple layers that are constructed of any suitable materials, including, but not limited to, glass, plastic, silica, Lexan™, acrylic, polycarbonate, or other clear material that does not impair vision, i.e. without impairing forward, lateral, close, distant or peripheral vision. In certain aspects the lenses 120 may be designed to be prescription eyewear, or accept within its frame prescription eyewear or fit over prescription eyewear. These lenses 120 may be clear in color, tinted dark, (e.g. darker tint for outdoor use, e.g. sunglasses), yellow, brown, or any other standard or custom color, or self adjusting (e.g. change color when moving to different environments based on user preference or ambient light) or designed for light or dark environments. They may be planar, curved, convex or concave, rigid or flexible in part in order to better protect the wearer's eyes. The lenses 120 in a preferred embodiment are formed together as to form a single clear plastic lens across ones face as well as part of the rim 110 (either through manufacturing or by bonding or snapping the lens to the rim 110), creating a permanent single piece that allows maximum visibility and does not have any noticeable separation from the rim 110 itself and can meet government standards consistent acceptable for use by first responders or the military (e.g. shooting a weapon, defending against airborne particles, blood splatter, etc.). In a further embodiment the lenses may carry a distinguished mark, design or marker, such as a symbol or design visible only by using infrared, night vision, prism, hologram or other type of device so as to be recognizable by such covert means. In other embodiments the lenses 120 are permanently attached to rim 110 with glue, screws, snaps, or other type of adhering medium (e.g. tape or sealant) that prevents dislodging. In other embodiments the lenses 120 may be removable so as to allow replacements after use, interchangeable (e.g. colored or clear) or have several layers (e.g. peel off plastic sheets) thus allowing the user to remove damaged or scratched panels that may impair vision. The rim 110 may or may not have a bridge 130, on one edge either as a design feature, a strengthening member, for stabilization, or as an attachment point and is made of a compatible material to the rim 110. In the preferred embodiment the bridge 130 is made of the same material of and formed as part of the top of the rim 100 so as to rest above the users nose at it's center point and is used as a support and attachment point as described below. Below the bridge lies the nosepiece 140, which is designed or formed, to rest on the user's nose and may have insertion holes 115 as described below. In a preferred embodiment the nosepiece is made of plastic or soft nylon and has pad plates 150 which are adjustable and made of a soft material (e.g. silicone) so as to provide a seal without irritating the skin of the user. Those skilled in the art will can appreciate that the pad plates 150 may be built into or formed as part of the nosepiece 140, and may be removable or replaceable.

End pieces 160 are located at the outer edge of the rim 100. In the preferred embodiment they are again formed and manufactured as part of the rim 100, are cylindrical and circular in form with and opening at the center point and designed to accept the hinged earpieces 170. The end pieces 160 may on the interior of their cylindrical opening have threads so as to accept a screw. The hinged earpieces 170 may be formed of a singular material (e.g. plastic or other copolymer) or be a combination of materials (e.g. plastic earpiece with an attached metal hinge). Regardless of design the hinged earpieces 170, which may also have threads on their innermost cylinders, are designed to insert and align into the end pieces 160 in a staggered alignment, which may be of equal or unequal number (e.g. two on one piece, one on the other, or two on each, etc.) so as to create a swinging hinge. It can be appreciated by those familiar with the art that when the hinged earpieces 170 are attached they swing open to a point whereby each side is perpendicular to the rim 100, and close to a point whereby they are nearly parallel to the rim 100 but angled at the hinge point in such a manner so that one hinged earpiece 170 does not interfere with the other. The end piece 160 is placed at a level on the rim 100 whereby when the nosepiece 140 rests on the user's nose and the hinged earpieces 160 are attached and open they rest comfortably above the user's ears. Once aligned the hinge created by the two pieces can be secured through the use of a pin, screw or other connecting adjunct.

The hinged earpieces 170 may be solid or hollow in nature and may have attachment points or inserts as defined below, and may be adjustable in both length and angle so as to accommodate the user. At their distal end are the curved bends 180 that are designed to take advantage of the natural curve of the pinna and assist in stabilization of the device 10 while being worn. Those familiar with the art can appreciate the curved bend 180 may not curve at all, be severe in angle so as to encircle the pinna, or be adjustable or bendable to account for the physical variations and characteristics of the user. The curved bend 180 may also contain an attachment point or points for a halyard or securing device across the back of one's head. In the preferred embodiment the curved bend 180 has a downward bend at the top of the pinna and is formed and manufactured as part of the hinged earpiece 170. In other embodiments they may be designed as an insert or attachment (e.g. slip on, glue on, snap on) or have a coating (e.g. rubber, silicone) that allows for friction and comfort by the user.

It should be appreciated that any of the aforementioned pieces may be coated, dipped or covered partially or fully to enhance the appearance of the frame 100, to allow for personalization or security, or as an adjunct for other uses (such as a solar panel covering).

In a further embodiment the frame 100 may carry within its parts a radio frequency identifier, transmitter, or other type of covert identifier for identification of the user. As an example the rim 110 may be hollow in nature so as to accommodate a wire antenna or receiver aid with a battery in the hollow of one hinged earpiece 170 and a radio frequency identification (RFID) tag in the other. A small light may be located on the frame 100 and when one user looks toward another the light may illuminate, or in other embodiments the lenses 120 may change color or present a prism, hologram or other identifier. In another embodiment the frame 100 may in one of its accessible cavities have a number or code that can be dialed or punched in by the user that would have to coordinate with other users in order to activate the signaling device. As an example in that manner several agencies (e.g. law enforcement and government and military) could be sent the code prior to meeting at a predetermined spot. Even if one of the devices had been compromised the person wearing it would have to also have the code to be recognized by others.

Another embodiment would allow for the presence of a sensing device built into the frame 100 and it's parts that would alert the user by means of vibration, light or sound the presence of a chemicals or high levels of vapors; or as a warning or danger signal initiated by means of a signal from another user (e.g. through RFID activation).

The facepiece cartridge 200 is a removable adjunct that attaches to the frame 100 to become the device 10 and is described below. The facepiece cartridge 200 consists firstly of the facepiece holder 210 which in a closed state is a hollow part consisting of two matching pieces that fit together (e.g. snap, glue or adhesive) or are joined by a line of weakness and has on it's innermost ridge insertion tabs 215 that are designed in the preferred embodiment to align with the insertion holes 115 on the rim 110 and nosepiece 140 and connect in a manner so as when put into place creates a tight tolerance which does not to allow an opening to the rim 110, and appears as if it is part of a conventional pair of eye glasses, sun glasses, or safety glasses. In other embodiments the facepiece holder 210 may attach by other means such as a hook and loop system, slide, adhesive, etc. Based on the design of the rim 110 the facepiece holder 210 may be rectangular, oval or circular in its circumference in such a manner as to be incorporated as an inconspicuous part of the device 10. To maintain an unobtrusive look it should be noted that parts of the rim 110 structure may be uneven so as to appear planar with the facepiece holder 210 attached and in the preferred embodiment is made of the same material as the rim 110, but in other embodiments may be made of rubber, plastic or other copolymers or substrates. At a central location on the top ridge of the closed facepiece holder 210 and comprised of similar material is the release tab 220 which is attached to the front portion of the piece and protrudes or angles slightly from a point centered with the nose piece 140 in such a manner to as to be accessible by the user with one (either) hand while wearing the device 10.

In the preferred embodiment the user grasps the release tab 220 by pinching it between a thumb and a finger with a small amount of pressure. This pressure (e.g. squeezing, twisting, or pulling, etc.) breaks or causes the line of weakness 225 that holds the two parts of the facepiece holder 210 together to separate (e.g. unsnap, tear, or break) into two pieces and causes the rear portion to remain attached to the rim 110 while the front section to moves in a outward manner revealing the facepiece 230; which is attached (e.g. glued, taped, caulked or inserted) permanently on the top and bottom end to the interior cavities of the two pieces. The facepiece 230 in the preferred embodiment is rectangular in nature in a size that will cover the nose, mouth and partial facial area of most users and is convex in an area to allow for facial features (e.g. nose) being covered while sealing at the sides of the face. It is constructed of a blend of cotton fibers, but may also be made of cloth, nylon, fiber, wool, Kevlar™, Gortex™, Teflon™, hemp, or any number of or types of blends of materials so as to provide filtering of air and inhibit the passing of particles or droplets (e.g. smoke, dust, pathogens, chemicals, etc.) into one's respiratory system through the nasal or pharyngeal orifices, and to inhibit irritation of the skin of the face. The facepiece 230 may have supporting or strengthening materials attached to or woven into it, such as nylon, spandex, carbon materials, Lycra™ fiberglass, Teflon™, Nomex™, Kevlar™, Aramid™ or other polymers, metal, braided metals, foils or other types of fibers. The facepiece 230 in further embodiments may be of any color and contain markers or materials that can be used as a distinguishing or safety feature. For example it may be treated with, contain, or have attached to it (e.g. litmus paper) a substance that causes the adjunct to change hue (i.e. turn blue) if exposed to certain types or specific amounts of chemicals. The facepiece 230 also can be imbedded with any number of chemicals or drugs to suppress pathogen infection, such as anti-bacterials, anti-virals, etc. Other embodiments include imbedded chemicals to avoid harm to the wearer, such as bases to neutralize acid contamination (e.g. chlorine gas contamination), acids to avoid base contamination, carbon compounds (such as carbon nanotubes, activated charcoal) etc., depending on the potential danger, where troops are deployed, etc. Neutralization or antagonist agents (e.g. against toxins) can also be used. In even further embodiments the deployed facepiece 230 may be imprinted (e.g. with a military, law enforcement, Red Cross, etc. logos) or contain markings such as a thread or line of threads visible only by the use of an adjunct (e.g. fluorescence, night or infra red vision goggles). In the preferred manner the facepiece 230 is collapsed accordion style so as be encompassed in the facepiece holder 210 until exposed and to deploy in the most advantageous way, but it may also be folded, compressed, rolled, stamped, or packed (e.g. vacuum or machine). Furthermore the facepiece 230 may be designed to deploy with a curtain effect or be custom molded as to allow for facial features (e.g. nose, chin, etc.) or in other embodiments be inflatable (e.g. a plastic edge inflated by a one way check valve that creates a seal).

Once deployed the facepiece 230 is pulled down (from the bottom of the rim toward the chin of the person wearing the device) in a single motion by means of the user maintaining their grip on the release tab then lowering over one's face it until it unfolds fully and resistance is encountered from the frame 100. Dependent on the size or physical characteristics of the user's head it may stop at the area of the user's chin or pass below it.

Once the facepiece 230 is fully deployed the securing strap(s) 240 are used to keep the facepiece close to the wearer's face. These adjuncts are general formed of a suitable material, including but not limited stretchable material such as rubber, elastic, spandex, Lycra™, hemp, cotton, wool, silicon, nylon, Kevlar, plastic, or other copolymer material, etc. In a preferred embodiment a flexible, stretchable, securing strap 240 is attached to lower end of the deployed facepiece holder 210 at or near a point where the edge of the facepiece 230 is adhered to it and wraps around the user's neck to an attachment point on the other end of the same piece. As the securing strap 240 retracts the tension pulls the facepiece 230 toward the user's face and helps to seal the unit in place. As those skilled in the art can appreciate there are multiple embodiments for attaching an adjunct such as this to one's face (e.g. mask, dust mask, filter) using one or more attaching strategies, including adhesive, self forming, metals, multiple straps, etc. In a further embodiment the securing straps 240 may be designed to attach to the hinged earpieces 170 on either side in such a manner as to be non obvious (e.g. as a decorative stripe) and drop down on either side of the user's face when the facepiece 230 is in place. In this embodiment they may be located at any desired place along the longitudinal axis of the hinged earpiece 170 to create the desired final location (e.g. in front of or behind the pinna), or in a further embodiment be attached to or pull out of the side or back of the curved bends 180. Another embodiment would allow the release tab 220 would be have the securing strap(s) 240 passing through it so that when the facepiece 230 has been deployed below the chin one could pull on the securing strap(s) 240 to tighten it while holding the release tab 220 and it would be held in place by means of a friction device (e.g. ball and spring pin or cleat).

Another embodiment for deploying and securing the facepiece 230 would entail having hidden or non obvious support piece section(s) 250 that are attached to the hinged earpiece (s) 170 at one end by a pivot point 255 which may be comprised of plastic, metal or composite (e.g. silicone, copolymer) and inter-connected to each other by means of connecting points 260 (e.g. hole or threaded port and screw, or plastic tab) and a joining connector 265 that is made of a flexible, stretchable or other compatible material. The inside edge of the support piece section(s) 250 are also attached to the facepiece 230. When the release tab 220 is activated the support piece sections(s) 250 unfold with the facepiece 230 in an accordion, scissor or other style in such a manner as to drop down in font of the pinna and in effect create a linear frame of the face of the user and also hold the facepiece 230 against the user's face by means of friction, memory bends, molding, adhesives, etc.

I claim:

1. A composition comprising an eye protection adjunct that provides protection to the eyes of a person and has a face protection system comprised of a facepiece holder and a facepiece that is deployable between a hidden position where the facepiece is hidden from view and an extended position to extend said facepiece a such that the facepiece protects the eyes, the face from the distal corners of the eye orbits to the distal corners of the mouth, and the nasal and pharyngeal openings of a person wearing said eye protection adjunct.

2. A composition according to claim 1 above where the composition further comprises normal eyewear.

3. A composition according to claim 1 wherein the facepiece is contained in a removable cartridge.

4. A composition according to claim 1 wherein said face protection system comprises stretchable material.

5. A composition according to claim 1 wherein said hidden facepiece is contained within a hollow cartridge that holds said hidden facepiece to inhibit inhaling particulates through the nasal and pharyngeal openings by a person.

6. A composition according to claim 1 wherein said facepiece is deployable with one hand.

7. A composition according to claim 1 wherein said facepiece changes color upon detecting chemicals or vapors.

8. A composition according to claim 1 wherein said facepiece contains a hidden identifier not visible to the human eye.

9. A composition according to claim 1 wherein said facepiece includes an embedded substance that acts as an antagonist against or neutralizes certain chemicals or pathogens.

10. A composition according to claim 1 wherein said facepiece has a coating that acts as an antagonist against or neutralizes certain chemicals or pathogens.

11. A composition according to claim 1 wherein said facepiece an electric interface that activates a signaling device.

12. A composition according to claim 1 further adapted to contain a radio frequency identifier tag that recognizes tags on similar devices.

13. A composition according to claim 1 wherein said face protection system has a flexible plastic frame.

14. A system comprising a composition according to claim 12 and further adapted to include a code system for setting an individual code to be recognized by others.

15. A method of protecting one's face as needed comprising wearing the composition of claim 1 and deploying said facepiece with one hand.

16. A composition according to claim 1 wherein said eye protection adjunct is selected from the group consisting of safety glasses, corrective lens glasses and sunglasses.

* * * * *